United States Patent [19]

Girimont

[11] Patent Number: 5,236,236
[45] Date of Patent: Aug. 17, 1993

[54] PROCESS AND IMPLEMENTS FOR CLEANING, RINSING, STORING AND INSERTING A CONTACT LENS

[76] Inventor: John V. Girimont, 6 Redstart Path, Hilton Head Island, S.C. 29926

[21] Appl. No.: 782,601

[22] Filed: Oct. 25, 1991

[51] Int. Cl.⁵ .............................................. A61F 9/00
[52] U.S. Cl. ..................................... 294/1.2; 206/5.1
[58] Field of Search .......................... 294/1.2; 206/5.1

[56] References Cited

U.S. PATENT DOCUMENTS

| | | | |
|---|---|---|---|
| 2,880,441 | 4/1959 | Rushing | 15/214 |
| 2,919,696 | 1/1960 | Rinaldy | 206/5.1 |
| 3,063,083 | 11/1962 | Obitts | 15/104.92 |
| 3,132,887 | 5/1964 | Martinez | 294/1.2 |
| 3,139,298 | 6/1964 | Grabiel | 294/1.2 |
| 4,088,359 | 5/1978 | Buchanan, Jr. | 294/1.2 |
| 4,167,283 | 9/1979 | Feldman | 294/1.2 |
| 4,200,320 | 4/1980 | Durham | 294/1.2 |
| 4,223,782 | 9/1980 | Giambalvo | 206/5.1 |
| 4,479,672 | 10/1984 | Jermyn | 294/1.2 |

FOREIGN PATENT DOCUMENTS 1401116 4/1965 France .............................. 294/1.2

Primary Examiner—Joseph D. Pape
Attorney, Agent, or Firm—W. C. Tupman

[57] ABSTRACT

A process for cleaning, rinsing, storing and inserting a soft, extended wear contact lens onto one's eye, all without touching the lens with the human hand. The implements for carrying out this process include a reverser, an inserter, a holder and a storage case. The inserter has an oval portion for holding a contact lens. This oval portion is also provided with a recessed area for determining the correct profile of a lens.

7 Claims, 4 Drawing Sheets

PROCESS AND IMPLEMENTS FOR CLEANING, RINSING, STORING AND INSERTING A CONTACT LENS

BACKGROUND OF THE INVENTION

Heretofore, soft, extended wear contact lenses were removed from and inserted onto the eye using one's fingers. The lens was cleaned and rinsed by using one's fingers while holding the lens in the palm of the other hand. This type of cleaning is extremely haphazard and can result eye infection or irritation, as well as damage to the lens itself.

Also, the profile of the lens was checked while pressing on the body of the lens with the thumb and forefinger of one's hand. Not only could this further contaminate the lens, but it was not uncommon for one to drop the lens while pressing, thus subjecting the lens to further damage.

As such, an object of this invention is to perform a process of cleaning, rinsing, storing and inserting a soft, extended wear contact lens onto one's eye without touching the lens with the human hand, thereby prolonging the life of the lens.

Another object of this invention is to provide a set of implements for performing the cleaning, rinsing, storing and inserting steps of the process.

Still another object of this invention is to provide means to readily determine the profile of a contact lens.

Other objects and advantages of this invention will become apparent from the following detailed description of the invention when considered along with the drawings.

BRIEF DESCRIPTION OF THE DRAWINGS

FIG. 14b discloses the step of applying the lens to my holder.

FIG. 14c discloses the step of cleaning the lens by scrubbing the lens with the scrubbing pad.

FIG. 14d discloses the step of retacting the slide of my holder so that my reverser may be inserted under the lens for removal thereof.

FIG. 14e discloses the step of removing the lens from the holder.

FIG. 14f discloses the step of applying the reverse side of the lens to the holder by use of my reversing implement.

FIG. 14g discloses the step cleaning the reverse surface of the lens by scrubbing.

FIG. 14h discloses the step of applying the cleaned lens into the storage case of my invention.

FIG. 14i discloses the position of the float after the step of filling the storage case compartment with storage solution.

FIG. 14j discloses the step of engaging the stored lens with the inserter of my invention after removing the storage solution from the storage case.

FIG. 14k discloses the position of the lens after the step of removing the lens from the storage case.

FIG. 14l discloses the step of inserting the lens into one's eye with the aid of my lens inserter.

DETAILED DESCRIPTION OF THE DRAWINGS

Figure 1:
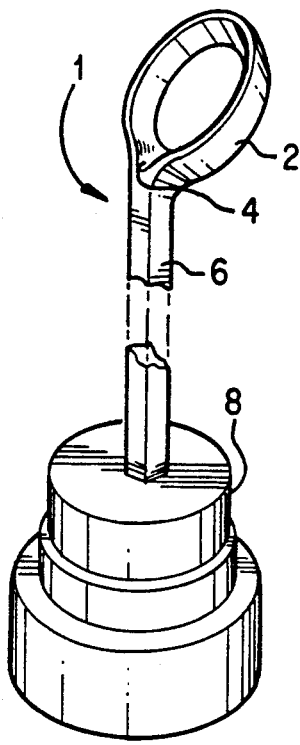
FIG. 1 is a perspective view of a lens inserter embodying the principles of the present invention.
Figure 4:
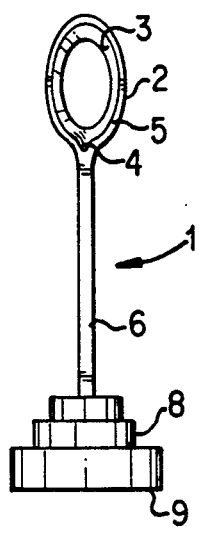
FIG. 4 is a front elevation view of the lens inserter.
Figure 14A:
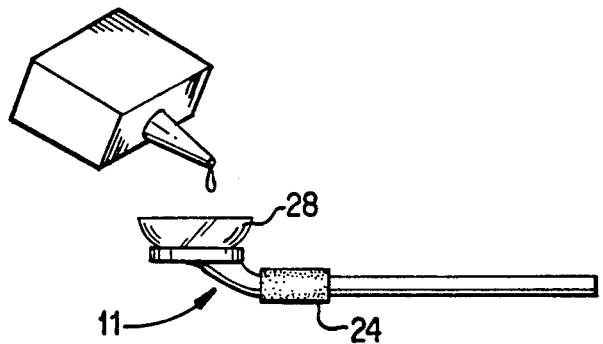
FIG. 14a-14l show the steps of my process for cleaning, rinsing, storing and inserting a contact lens, wherein FIG. 14a discloses the step of holding the lens in my reversing implement while applying a rinsing solution.

Referring to the drawing,

FIG. 1 shows the inserter implement of my invention. This implement is composed of two distinct parts; one being the stem 6 and loop 2, while the base 8 constitutes the other part. As best shown in FIG. 4, the loop 2 is oval shaped with its inner surface 3 being inwardly beveled. By beveling this surface, the area of contact between the implement 1 and a soft contact lens 28 is increased. This relationship is best shown in FIGS. 14k and 14l.

Another feature of the inserter 1 is the presence of a notch or recess 4 located at the base of the loop 2. The notch or recess 4 of the loop is in the form of a recessed area, thus providing an indentation or a depressed portion with respect to the remaining inner surface 3 of the loop 2. The notch or recess 4 extends at least to the surface 5 of the loop 2 and may extend along the entire width of the inner surface 3 toward the opposite surface 7 of the loop. This recess or notch is useful in enabling one to determine whether or not the lens is in its correct profile. This can easily be ascertained by adding a couple of drops of a saline solution or the like to the lens 28 while the lens is held in the inserter 1.

Figure 7:
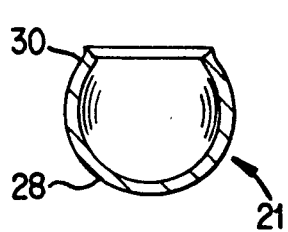
FIG. 7 is a cross-sectional view of a lens whose profile is correct.

FIG. 7 shows the lens 28 in its correct profile, since the edge 30 of the lens is slightly inwardly directed.

Figure 8:
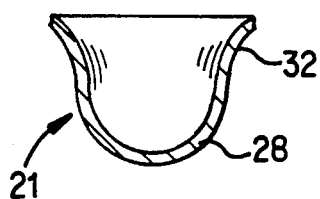
FIG. 8 is a cross-sectional view of a lens whose profile is incorrect.

FIG. 8 shows an inverted lens 28 whose curvature has been reversed and thus presents an incorrect profile. This is readily indicated by the fact that edge of the lens is outwardly flared at 32.

Figure 2:
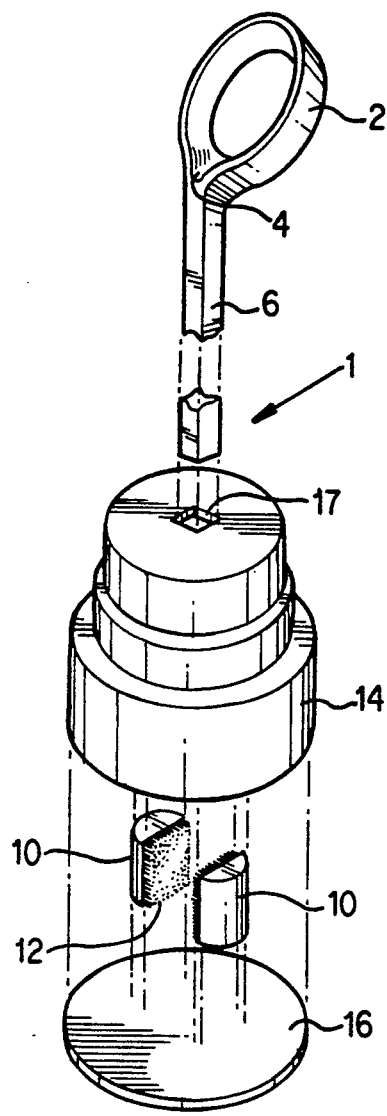
FIG. 2 is an exploded perspective view of a disposable lens inserter and a permanent holder.

The base 8 of the inserter 1 comprises a plurality of disc shaped elements. The largest disc shaped element is shown in FIG. 2 at 14. These disc elements are of a sufficient size to snugly fit the opening of a vial (not shown) thus enabling the inserter 1 to be stored in a sealed container. Instead of a snug, press fit, an appropriate screw thread connection may be used between the base 8 and a storage container. The end portion 9 is sufficiently large to permit the inserter 1 to easily stand on a surface in the upright position of FIGS. 3 and 4 when not in use. The base 8 serves as a handle when using the inserter 1 to place a contact lens on one's eye.

Another feature of the inserter 1 is best shown in FIG. 2. Here the stem 6 is detachably connected to the base 8 and is thus disposable. A pair of inserts 10 are adhesively secured within the base 8. Member 16 covers the inserts 10 and is the end piece of the base 8. The inner surface of the inserts are provided with inwardly directed fiber members 12. The inserts are spaced apart a distance substantially equal to the width of the stem 6, so that the stem 6 is removably held in place by a frictional engagement of the fiber members 12. Opening 17 in the base 8 is sufficiently large to permit the stem 6 to be easily removed or inserted.

Figure 3:
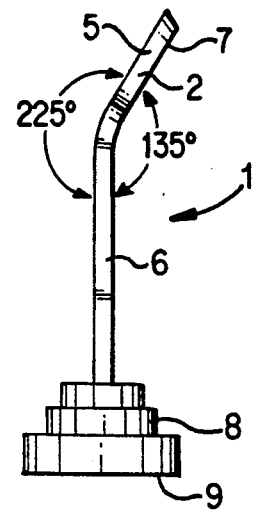
FIG. 3 is a side elevation view of the lens inserter.

As shown in FIG. 3, the loop 2 of the inserter 1 extends from the stem 6 at an angle of approximately at an angle with respect to the stem 6. This angle is approximately 225° between the side surface 5 of the loop 2 and the stem 6 or approximately 135° between the other side surface 7 of the loop 2 and the stem 6. As such, the loop 2 extends at an obtuse angle with respect to the stem 6. The surface 5 is on the convex side of this angle, while the surface 7 is on the concave side. As indicated by FIG. 14*l*, this angled relationship enables one to easily insert the lens 28 into the eye without any interference from the stem 6.

Figure 5:
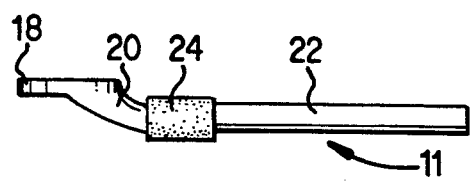
FIG. 5 is a side elevation view of a lens reversing implement of this invention.
Figure 6:
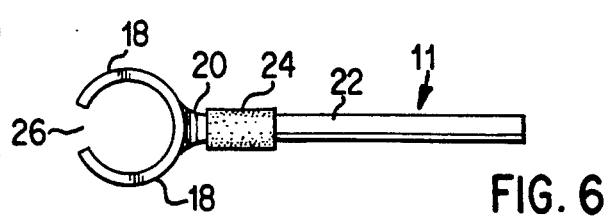
FIG. 6 is a top elevation view of the lens reversing implement.

A reversing implement 11 is shown in FIGS. 5 and 6 and comprises a loop 18 connected to an elongated stem 22 by an intermediate flange 20. The loop 18 is opened at 26. The opening 26 enables the loop 18 to straddle the part 46 of a holder 41 at a position below a lens so that the lens may be readily removed from the holder. This relationship is best shown in FIG. 14*d*.

As shown in FIG. 5, the outer surface of loop 18 is offset laterally from the stem 22. This permits a lens 28 to be carried within the loop, as shown in FIG. 14*a*, or to be carried over the loop, as shown in FIG. 14*e*. By supporting the lens 28 on either its concave side or its convex side enables the implement to be used in reversing the position of the lens on a holder 41. The reversing steps are best shown in FIGS. 14*b*, 14*d*, 14*e* and 14*f*.

A scrubbing pad 24 is carried on the stem 22 of the reversing implement 11. The pad 24 is made from a soft foam material or the like and must be capable of holding saline and cleaning solutions. FIGS. 14*c* and 14*g* show the use of pad 24 as a scrubber for cleaning both surfaces of a lens 28.

Figure 9:
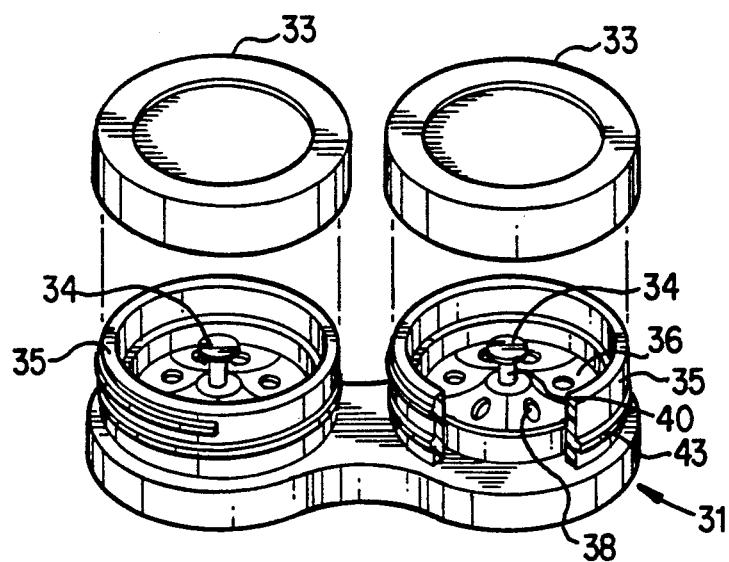
FIG. 9 is an exploded perspective view of a storage case for a pair of contact lenses according to the invention.
Figure 10:
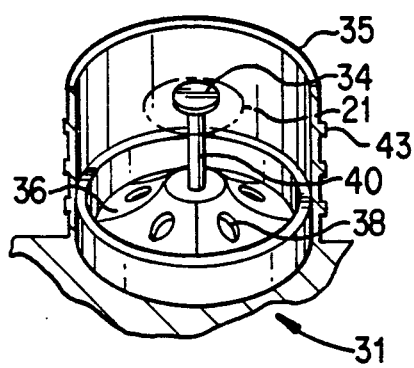
FIG. 10 is a partial cross-sectional view of a single compartment of the storage case with the float in its lower position.
Figure 11:
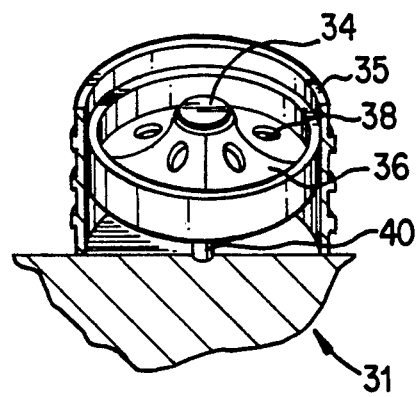
FIG. 11 is a partial cross-sectional view of a single compartment of the storage case with the float in its raised position.

The storage case 31 is best shown in FIG. 9, 10 and 11 and comprises a pair of compartments 35 connected by a common base. Each compartment 35 is provided with a separate cover 33 which may be secured in place by means of the screw threads 43. Centrally positioned within each compartment 35 is an enlongated stem 40 which terminates in a flat pad 34 at its upper end.

A float 36 is also carried in each compartment 35. Each float 36 is slideably positioned about the stem 40 and is made of a material of sufficiently low density that will enable the float 36 to readily rise to the upper surface of any storage fluid placed within the compartment 35. Either a saline solution or a suitable sterilizing solution may be used for this purpose. Openings 38, which extend completely through the float 36, also aid in permitting the float to rise. The pad 34 acts as stop for the float 36. FIGS. 9 and 10 show the float at the bottom of the compartment 35, while FIG. 11 shows the float in its fully raised position in engagement with the pad 34.

The upper surface of the float 36 is dome shaped and thus aids in supporting a lens 28 for storage purposes.

The pad 34 is flat in order to minimize the amount of contact between the lens 28 and the pad. This minimal contact becomes critical as best shown in FIG. 14*j* when the inserter is used to lift the lens 28 out of the storage case. The beveled surface 3 of the inserter provides greater surface contact with the lens 28 than does the peripheral edge of the pad 34. With the float 36 in its lower position, the surface tension between the inserter 1 and the lens 28 is therefore greater than the surface tension between the pad 34 and the lens. Thus, the lens 28 may easily be lifted from the case 31. The diameter of the pad 34 should be approximately one-half the diameter of the opening of the lens 28 at its edges. If the pad 34 is too small, the lens will flop down around the post when the float is lowered. If the pad 34 is larger, the resistance against lifting the lens with the inserter 1 is increased and made difficult. Also with a larger pad 34, the beveled surface 3 of the lens will make less overall contact with the lens 28, thus reducing the surface tension.

While not shown in the drawings, the underside of the cover may be provided with an inwardly extending, dome shaped member which is centrally attached to the center of the cover. The inner surface of this dome member has a concave surface and may be provided with a plurality openings extending completely through its surface. These openings would correspond very closely to the openings 38 in the float 36 and obviously would permit any fluid in the compartment 35 to easily pass through the dome. A pad member may be centrally positioned on the dome's inner surface. With the cover 33 fully secured on its compartment 35, the dome member would tend to clamp the lens 28 against the pad 34 and the float 36, thereby more securely holding the lens in place.

Figure 12:
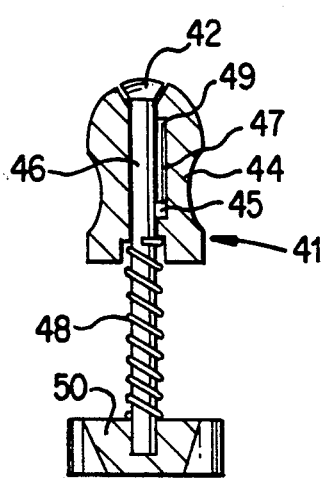
FIG. 12 is a cross-sectional front view of the lens holder of my invention with the slide in its raised position.
Figure 13:
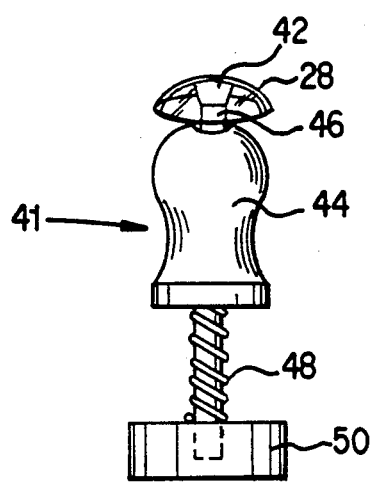
FIG. 13 is a front elevational view of the lens holder with the slide in its retracted position.

The holder 41 is shown best in FIGS. 12 and 13 and comprises a flat bottomed base 50 with an elongated stem 46 projecting upwardly from the base 50 and terminating in an outwardly flared end at 42.

A slide 44 surrounds the stem 46 and is free to move axially along the stem. The upper end of the slide 44 is outwardly flared in manner closely corresponding to the flared end 42, thus providing a stop for the upward movement of the slide. A spring 48 is positioned around the lower portion of the stem 46 and forces the slide 44 outwardly into engagement with the flared end 42. FIG. 13 shows the slide 44 in a partially retracted position, while FIG. 14*d* shows the slide in a fully retracted position. The outer surface of the slide 44 is circumferentially recessed intermediate its ends to provide a good finger grip when the slide is to be retracted. With the slide 44 in its upper position of FIG. 12, the holder 41 can readily support a lens 28 for scrubbing and rinsing. With the slide 44 fully retracted, as in FIG. 14*d*, the reversing implement 11 can easily be inserted around the stem 46 at a location under the lens 28 so that the lens may be removed from the holder without being touched.

Another means to stop the upward movement of the slide 44 about the stem 46 comprises a laterally positioned key 45 integral with the stem 46 and projecting into slot 47 on the inner surface of the slide 44. Engagement of that part of the slide 44 which defines the lower end of the slot 47 provides a stop for the upward movement of the slide along the stem. Likewise, the upper edge of the slot 49 limits the downward movement of the slide 44 by engagement with the key 45.

FIGS. 14a through 14l depict the various steps of the process for cleaning, rinsing, reversing, storing and inserting the lens onto one's eye without touching the lens by using my implements.

FIG. 14a shows the lens 28 supported by reversing implement 11 while being rinsed with a suitable solution. The lens 28 may be removed from one's eye with one's fingers and then placed on the reverser 11. At this point, the lens would never be touched again until it is to be removed once again from the eye.

Figure 14B:
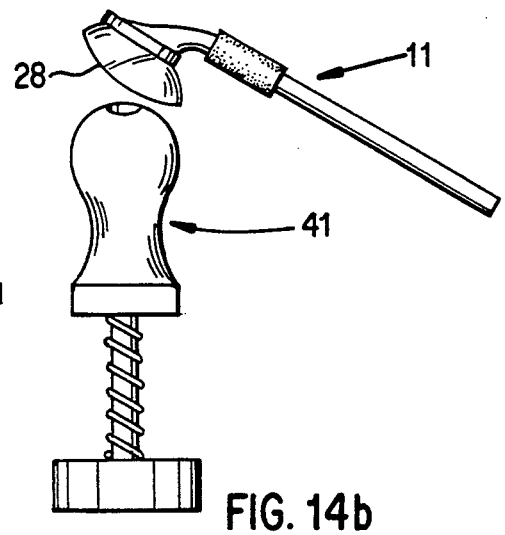
Figure 14C:
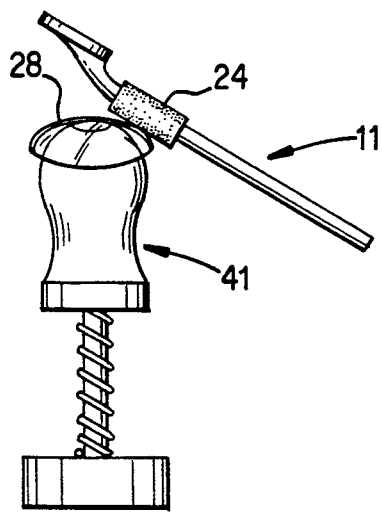
Figure 14D:
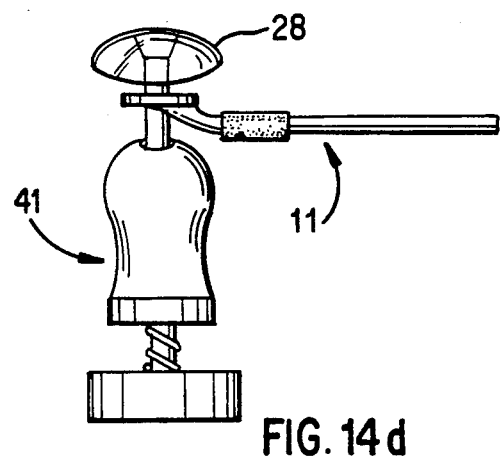
Figure 14E:
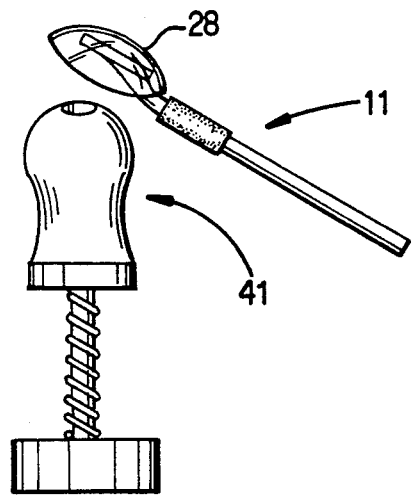

FIG. 14b shows the lens 28 being placed on the upper end of the holder 41. The lens 28 is retained on the reversing implement 11 by surface tension from the rinsing solution. This holds true even though the reverser 11 is inverted.

FIG. 14c shows the first surface of the lens 28 being cleaned by using the scrubbing pad 24 in conjunction with a suitable cleaning solution. The holder 41 is able to support the lens during this step.

FIG. 14d shows the slide 44 of holder 41 in its retracted position with the reversing implement 11 in position under the lens 28 and ready to lift the lens off the holder.

FIG. 14e shows the slide 44 of the holder in its upper position and the lens 28 being supported by the reverser 11. In this position, the concave surface of the lens covers the loop 18 of the reverser 11.

Figure 14F:
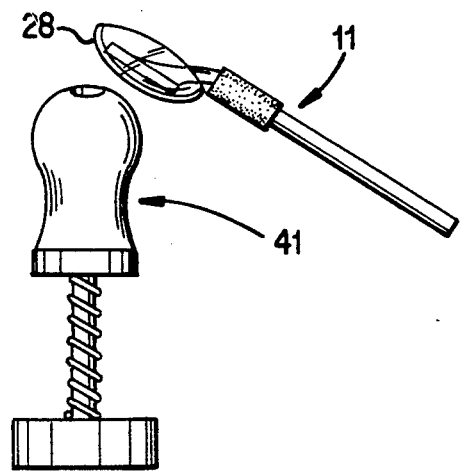
Figure 14G:
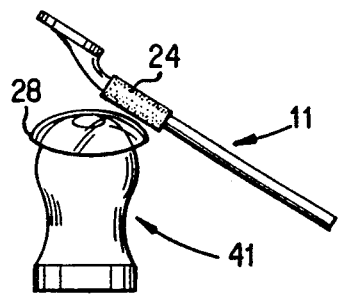

FIG. 14f shows the reverser 11 inverted with the lens 28 being held thereon by surface tension and about ready to again be placed on the holder 41.

FIG. 14g shows the other surface of the lens being cleaned by use of the scrubbing pad 24. It is understood that the lens 28 may be rinsed at any time it is supported on the holder 41 or held by the reverser 11.

Figure 14H:
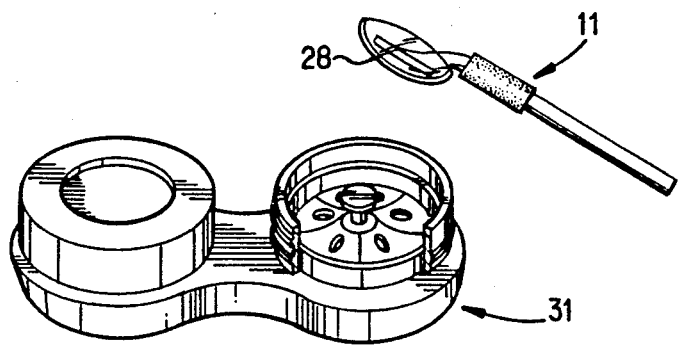

FIG. 14h shows the fully cleaned lens 28 about to be placed on the pad 34 of the case 31. While the profile of lens 28 is now in its incorrect position, this profile will change once the lens is placed on the pad 34 and released from the reverser 11.

Figure 14I:
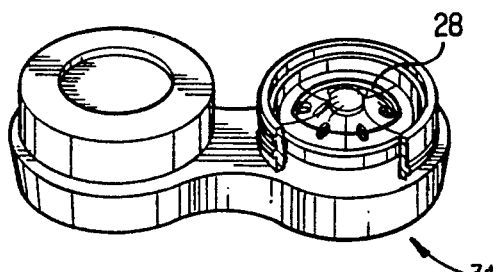
Figure 14J:
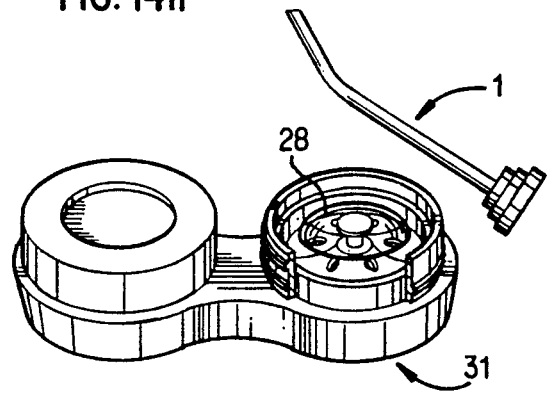
Figure 14K:
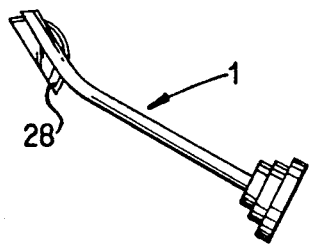
Figure 14L:
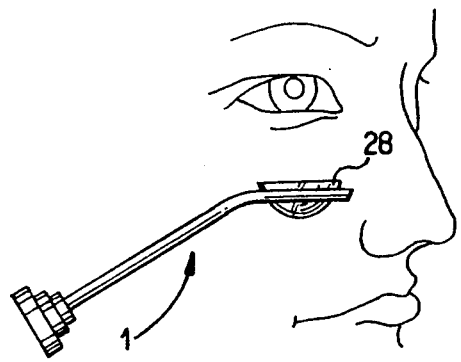

FIG. 14i shows the lens 28 in the storage case 31 with the compartment 35 having been filled with a suitable storage fluid, thereby raising the float 36 to its upper supporting position. The lens 28 is in its correct profile in this position.

FIG. 14j shows the lens 28 about to be removed from the storage case by the inserter 1. The storage solution has been removed from the compartment 35 and the lens is supported solely by the pad 34.

FIG. 14k shows the lens 28 being picked-up by the inserter 1 from the pad 34. This is accomplished by the fact that surface tension is greater between the lens 28 and the inserter 1 than between the lens and the pad 34.

FIG. 14l shows the lens 28 about to be inserted onto one's eye. A last check for a correct lens profile may be made before insertion by applying a couple of drops of rinsing solution or the like and then visually checking the profile of the lens.

Since various changes may be made in the construction of the implements and the process itself without departing from the scope of my invention, it is intended that all matter contained in the foregoing description and shown in the accompanying drawing shall be interpreted as illustrative only.

I claim:

1. A soft contact lens inserting implement comprising an elongated stem portion terminating at one end in an oval loop portion, said loop portion having an inner surface and a recessed area located along said inner surface adjacent to said terminal end of the stem, said recessed area extending to at least one side surface of said loop portion, whereby the correct profile of the lens may be readily determined with a lens being held within the loop portion of the implement in engagement with said recessed area thereof, thus permitting a lens to be properly inserted into one's eye while being held by said implement.

2. A soft contact lens inserting implement of claim 1, comprising a handle member located at the other end of said stem.

3. A soft contact lens inserting implement of claim 2, comprising means to removably attach said stem to said handle member.

4. A soft contact lens inserting implement of claim 2, wherein said handle member is shaped to fit the open end of a storage container.

5. A soft contact lens inserting implement of claim 1, wherein said loop portion extends at an angle obtuse with respect to said stem portion.

6. A soft contact lens inserting implement of claim 5, wherein said one surface of said loop portion is located on the convex side of the angle between the loop portion and the stem portion.

7. A soft contact lens inserting implement of claim 1, wherein said inner surface of the loop is at an angle greater than 90° with respect to said one side surface, thus providing a beveled inner surface.

* * * * *